(12) United States Patent
Jones

(10) Patent No.: US 8,534,300 B2
(45) Date of Patent: Sep. 17, 2013

(54) METHOD OF IMPLANT FLOSSING

(71) Applicant: Alexander Jones, Morrison, CO (US)

(72) Inventor: Alexander Jones, Morrison, CO (US)

( * ) Notice: Subject to any disclaimer, the term of this patent is extended or adjusted under 35 U.S.C. 154(b) by 0 days.

(21) Appl. No.: 13/732,549

(22) Filed: Jan. 2, 2013

(65) Prior Publication Data

US 2013/0118519 A1 May 16, 2013

Related U.S. Application Data

(63) Continuation of application No. 13/251,518, filed on Oct. 3, 2011, now abandoned.

(60) Provisional application No. 61/477,677, filed on Apr. 21, 2011.

(51) Int. Cl.
*A45D 24/00* (2006.01)
*A61C 15/00* (2006.01)

(52) U.S. Cl.
USPC ............ 132/200; 132/323; 132/321; 132/324

(58) Field of Classification Search
USPC ................. 132/320, 323, 324, 326, 327, 328, 132/329, 333, 309, 200, 325, 321, 322; 223/99, 223/102; 433/148, 149, 39; 606/148, 150, 606/225; 112/224, 225; D28/65, 66, 68
See application file for complete search history.

(56) References Cited

U.S. PATENT DOCUMENTS

| | | | | |
|---|---|---|---|---|
| 3,929,144 A | * | 12/1975 | Tarrson et al. | 132/323 |
| 4,016,892 A | * | 4/1977 | Chodorow | 132/323 |
| 4,064,883 A | * | 12/1977 | Oldham | 132/321 |
| 4,103,631 A | * | 8/1978 | Gray | 112/80.05 |
| 4,133,339 A | * | 1/1979 | Naslund | 132/323 |
| 4,330,014 A | * | 5/1982 | Glass et al. | 132/321 |
| 4,342,324 A | * | 8/1982 | Sanderson | 132/324 |
| 4,364,380 A | * | 12/1982 | Lewis | 433/18 |
| 4,832,063 A | | 5/1989 | Smole | |
| 4,947,880 A | * | 8/1990 | Tarrson et al. | 132/329 |
| 5,050,625 A | | 9/1991 | Siekmann | |
| 5,183,063 A | * | 2/1993 | Ringle et al. | 132/321 |
| 5,289,836 A | | 3/1994 | Peng | |
| 5,311,889 A | * | 5/1994 | Ringle et al. | 132/321 |
| 5,392,794 A | * | 2/1995 | Striebel | 132/324 |
| 5,566,691 A | * | 10/1996 | Dolan et al. | 132/321 |
| 5,638,841 A | * | 6/1997 | Levine | 132/323 |
| 5,735,299 A | * | 4/1998 | Kaltenbach | 132/323 |
| 5,799,673 A | * | 9/1998 | Amendola et al. | 132/321 |
| 5,890,500 A | | 4/1999 | Mabon | |
| 5,947,132 A | * | 9/1999 | Swanson | 132/321 |
| 6,065,176 A | * | 5/2000 | Watanabe et al. | 15/167.1 |

(Continued)

*Primary Examiner* — Vanitha Elgart
(74) *Attorney, Agent, or Firm* — Danel Boudwin

(57) ABSTRACT

A dental hygiene threading tool used to insert floss between teeth of a user who has permanent oral implants. Traditional flossing for individuals with oral implants and the methods of flossing between implants and the gum line presently available are time consuming and difficult, due to the lack of the space between the two structures. The disclosed device comprises a hollow tube used to guide a floss threading line or pull through guide into these tight spaces. The tube is then removed once the threading line has been inserted. A user feeds a strand of dental floss through the threading line loop and pulls the threading line with the dental floss through the space. Once the dental floss has been fed through the teeth, the flossing procedure may commence. The device dramatically reduces time and effort required to thread floss between teeth and oral implants.

4 Claims, 2 Drawing Sheets

(56) References Cited

U.S. PATENT DOCUMENTS

| | | | |
|---|---|---|---|
| 6,814,086 B2 * | 11/2004 | Stallings | 132/321 |
| 8,061,372 B1 * | 11/2011 | Allen | 132/329 |
| 8,127,778 B1 * | 3/2012 | David | 132/321 |
| 2005/0279377 A1 * | 12/2005 | Sarjeant | 132/321 |
| 2009/0277934 A1 * | 11/2009 | Youngman | 223/99 |
| 2011/0226279 A1 * | 9/2011 | Thorne | 132/323 |

* cited by examiner

METHOD OF IMPLANT FLOSSING

CROSS REFERENCE TO RELATED APPLICATION

This application claims the benefit of U.S. Provisional Application No. 61/477,677 filed on Apr. 21, 2011, entitled "EZ Time Saver Implant Flossing Guide Tube" and U.S. Non-Provisional Utility patent application Ser. No. 13/251,518 filed on Oct. 3, 2011, entitled "Implant Flossing Guide." For the purposes of providing a clear and continuous disclosure, the aforementioned applications are incorporated herein by reference.

BACKGROUND OF THE INVENTION

1. Field of the Invention

The present invention relates to dental hygiene tools for use by individuals with oral implants. More specifically, the present invention is a floss guiding device designed to assist a user in directing a dental floss threading line into the tight spaces between the user's gum line and his or her oral implant so that a user can feed a strand of dental floss into said space to facilitate effective flossing of the user's teeth and gums around the dental implant.

2. Descriptor of the Prior Art

Poor dental health can lead to a myriad of dental problems. In particular, inadequate or improper flossing can lead to bacteria and plaque buildup around the base of teeth and gums. Gum disease (periodontal disease) is a common result of improper dental flossing, as too is bad breath and gingivitis. Untreated gum disease can lead to gum damage and further oral complications. Proper dental care is important to an individual's overall health and frequent, proper dental flossing is an important part of maintaining good dental hygiene.

Some individuals have dental implants designed to keep their teeth straight, such as braces or permanent retainers. While these implants serve a cosmetic purpose, they often times impact the individual's ability to floss around those teeth that are impacted by the implant. Some implants are cemented against the backside of the teeth, making flossing those teeth a challenge. These types of implants typically lie across several teeth at once, parallel to the gum line, making it difficult to guide dental floss between the teeth and down to the gum line, since the implant lies therebetween. Other dental implants also require flossing care. For example, individuals with dental bridges and dentures are required to floss the area between the implant and the gum line.

Several patents have been granted to devices that attempt to provide users with a means of flossing between their gum line and an oral implant device or prescribes a means of flossing between teeth where an implant prevents flossing the area in a traditional fashion. These prior art devices have several known drawbacks. For example, with the exception of U.S. Pat. No. 4,832,063, each of the identified prior art patents addresses a user's need to floss between teeth, rather than under an implant such as a bridge or denture. Regardless of what area requires flossing, each prior art device requires the user to insert a floss guiding mechanism of some sort through the small space between the teeth and/or under the implant in order to feed a strand of dental floss through the space for a user to floss with. A common problem shared by these prior art devices is the usefulness of each device when the space requiring flossing is too small to accommodate the floss guiding mechanism.

U.S. Pat. No. 5,890,500 to Mabon describes a floss guiding tube for use by individuals who have a dental implant that spans across several teeth; for example, braces or a permanent retainer. The device comprises a small tube which can be inserted in between teeth. The user will feed a strand of dental floss through the tube, and then insert the tube between two of the teeth where an implant prevents the easy use of dental floss. The user must insert the tube between the teeth below the implant, close to the gum line. Once the tube has been inserted, a user can grab onto the strand of dental floss that has been fed through the tube and is now located on the inside of the user's mouth, through the teeth and under the implant close to the gum line. The user will pull back the tube so that the dental floss can make contact with the teeth and gum line and the user will floss in the traditional fashion. Once the user has finished flossing between these two teeth, the user will release the end of the dental floss which is located inside the user's mouth and pull the floss out from between these teeth.

The key to the Mabon device is that the user should not remove the tube from the strand of dental floss after he or she has inserted the tube between the teeth and under the implant, because then the user would have to rethread the tube floss guiding device again in order to floss in between the next pair of teeth. By keeping the floss guiding tube device on the strand of dental floss while flossing—but out of the way while flossing—the user can simply release the end of the dental floss that has been fed through the teeth by the floss guiding tube device, pull the floss out from the freshly flossed teeth and then reset the device quickly and easily to floss the next pair of teeth.

The Mabon device depends on the fact that the floss guiding tube can fit into the space between the teeth and beneath the implant. If the space is too small to accommodate the floss guiding tube, then the device will not function as intended and provide little utility for the user. The present invention is designed to accommodate even the smallest of spaces between teeth.

Another dental floss guiding device is described in U.S. Pat. No. 5,050,625 to Siekmann which describes a dental floss threading device for use by individuals with permanent dental implants. The device is an elongated tube having a handle on one end and a threading end with a decreasing diameter terminating in a point at the other. The threading end of the tube, which has the decreasing diameter, also exhibits a compressing of the tube so that the device gets smaller and flatter until reaching the pointed tip. The tube holds inside of it a predetermined amount of dental floss. One end of the dental floss protrudes from the pointed tip of the threading end of the device. The threading end is curved and is used for threading the dental floss between teeth and under a dental implant, while the user holds the device by its handle end.

A user would use the Siekmann device to feed a strand of dental floss in between those teeth that are impacted by a permanent dental implant. The user will stick the threading end of the device all the way through the teeth and yet under the implant so that the threading end of the device is accessible from the inside of the user's mouth. Once the threading end of the device is accessible, a user can grab the protruding piece of dental floss from the device and pull the device out from between the teeth leaving a strand of dental floss in its stead. The user would floss the area in between the teeth and then pull the dental floss back out through the front of the teeth when finished. The user would repeat the process with each pair of teeth which requires flossing that is impacted by the implant.

U.S. Pat. No. 5,289,836 to Peng describes a method for making a dental flossing device comprising a small guide post which is attached to a strand of dental floss. The guide post is a small, thin guide with one end attached to a strand of dental floss and the other end curved slightly. The user would feed the guide post under the implant and between the two teeth which require flossing. The guide has to be pushed all the way through the space between the teeth in order for the user to be able to use the dental floss effectively. The Peng device provides a guide that must fit completely through the space between the teeth and under the implant in order to be used effectively. Some users may be face with the problem that the space between the teeth and under the implant is too small to allow the Peng device guide post to go all the way through the space. The present invention implements the use of a very thin threading line that is fed through the space between the teeth and under the implant. The threading line is then used to pull a strand of dental floss through the space, enabling the user to effectively floss the area no matter how tight the space.

U.S. Pat. No. 4,832,063 to Smole describes an elongated version of the same concept described in the Mabon patent. The Smole device is an elongated floss guiding tube designed to be inserted between the teeth and under an implant. A user would insert the device between the teeth, but then feed the tube back between an adjoining pair of teeth from the inside of the user's mouth. The user will pull the floss guiding tube through the teeth leaving behind a strand of dental floss for the user to grab onto and use for flossing purposes. Again, like the Mabon device, the effectiveness of the device depends on whether the elongated floss guiding tube can fit into the space between the teeth and beneath the implant. If the space is too small to accommodate the elongated floss guiding tube, then the device is useless to the user. The present invention is designed to accommodate even the smallest of spaces between teeth.

It is therefore submitted that the present invention substantially diverges in design elements from the prior art, and consequently it is clear that there is a need in the art for an improvement to existing dental hygiene tools used by those with permanent dental implants for inserting floss between those teeth where traditional flossing is affected by the existence of a dental implant. In this regard the instant invention substantially fulfills these needs.

SUMMARY OF THE INVENTION

In view of the foregoing disadvantages inherent in the known types of dental flossing guides and tools now present in the prior art, the present invention provides a new dental floss threading tool wherein the same can be utilized for providing convenience for the user to use during flossing around and under a permanent dental implant, even when the spaces that require flossing are very tight.

It is therefore an object of the present invention to provide a new and improved dental floss threading device that has all of the advantages of the prior art and none of the disadvantages.

Another object of the present invention to provide a dental floss threading device that is designed to accommodate the feeding of a strand of dental floss between the teeth and/or gums of a user and a permanent dental implant.

Another object of the present invention is to enable a user to floss even the tightest spaces between teeth and dental implants.

Yet another object of the present invention is to provide users with a time saving and convenient means for flossing around dental implants.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
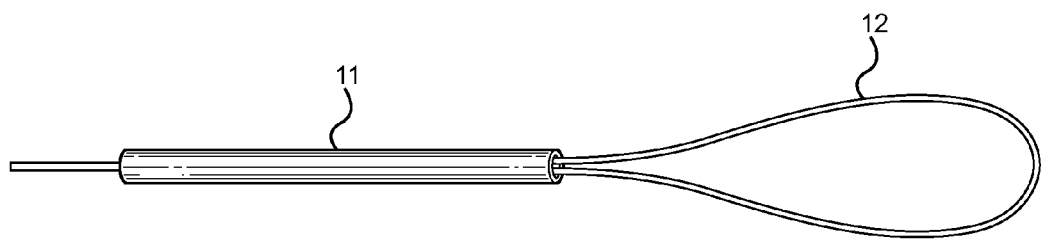
FIG. 1 is a perspective view of the present invention, wherein a floss threading line is placed into a guide tube.

Reference is made herein to the attached drawings. Like reference numerals are used throughout the drawings to depict like or similar elements of the dental floss threading device. For the purposes of presenting a brief and clear description of the present invention, the preferred embodiment will be discussed as used for improving one's ability to thread a floss threading line into a tight space between teeth or under a row dentures. The figures are intended for representative purposes only and should not be considered to be limiting in any respect.

Referring now to FIG. 1, there is shown a perspective view of the dental floss threading device of the present invention. The device comprises of a length of floss threading line 12 having a looped end and a closed end, along with a flexible tube handle 11 adapted to accept the closed end of the threading line 12. The flexible tube handle 11 is comprised of a thin flexible material that is malleable in operation and not prone to abrading the gum line of a user. Material contemplated for its construction include, but are not limited to, polyurethane, latex or similar plastic or polymer material. The floss threading line 12 is fed through the tube handle 11 prior to insertion into the oral cavity of a user. The floss threading line is comprised of a sturdy composition and sufficient stiffness such that it retains its shape during insertion into a user's mouth, but is flexible enough to be pulled between the teeth and through tight spaces. The floss threading line may be made from a thin fiber of plastic but it is not desired to limit its composition to a specific material.

Figure 2:
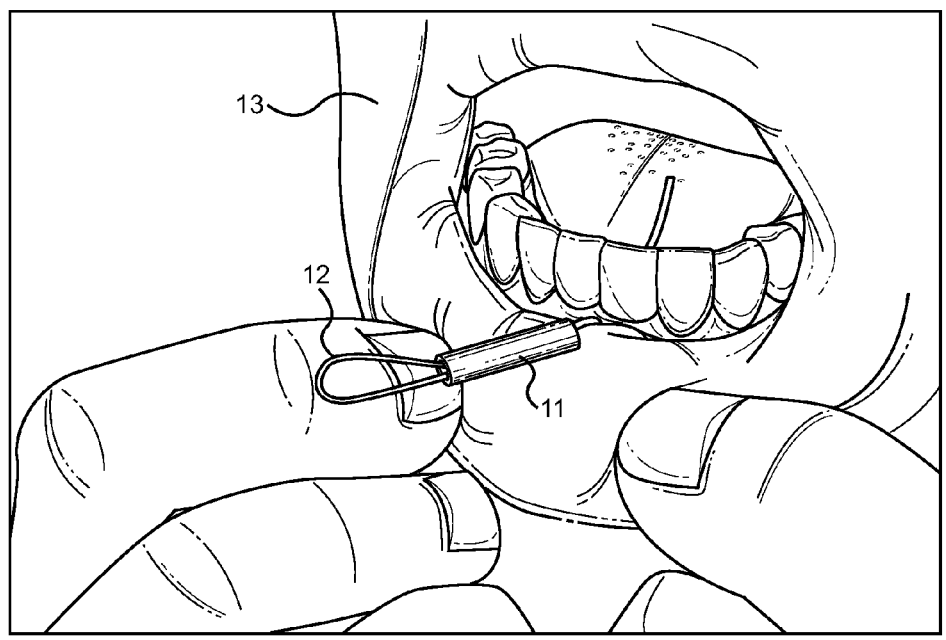
FIG. 2 is a perspective view of the present invention after a user has inserted the closed end of the threading line into a space between the user's dentures and gum line.

Referring now to FIG. 2, there is shown a perspective view of the present invention in use by an individual. To use the device, a user 13 places the floss guiding tube 11 up to an open space wherein the floss threading line 12 is to be inserted between the user's dentures and gum line. The threading line 12 is inserted from the front side of the user's teeth. The non-loop end is the end is inserted into the space that requires flossing for later pull-through of a length of dental floss, which facilitates its entry through tight spaces between teeth or below a row of dentures. For spaces that are large enough to accommodate the user inserting the floss guiding tube 11 into the space, users may use the device in this way. However, for spaces that are smaller, users place the floss guiding tube 11 up to the space and gently force the floss threading line 12 through the space.

The tube serves as a guide, preventing the threading line from straying from its intended destination. The threading line has a composition of sufficient stiffness in order to hold its shape while being guided through the space and the tube aids in the guidance of the threading line. Once the threading line is placed through the space requiring flossing, the user may grasp the threading line and pull it further through until the non-loop end of the threading line is approximately half way inside the user's mouth and the loop end of the threading line and the guiding tube are still located outside of the user's mouth.

Figure 3:
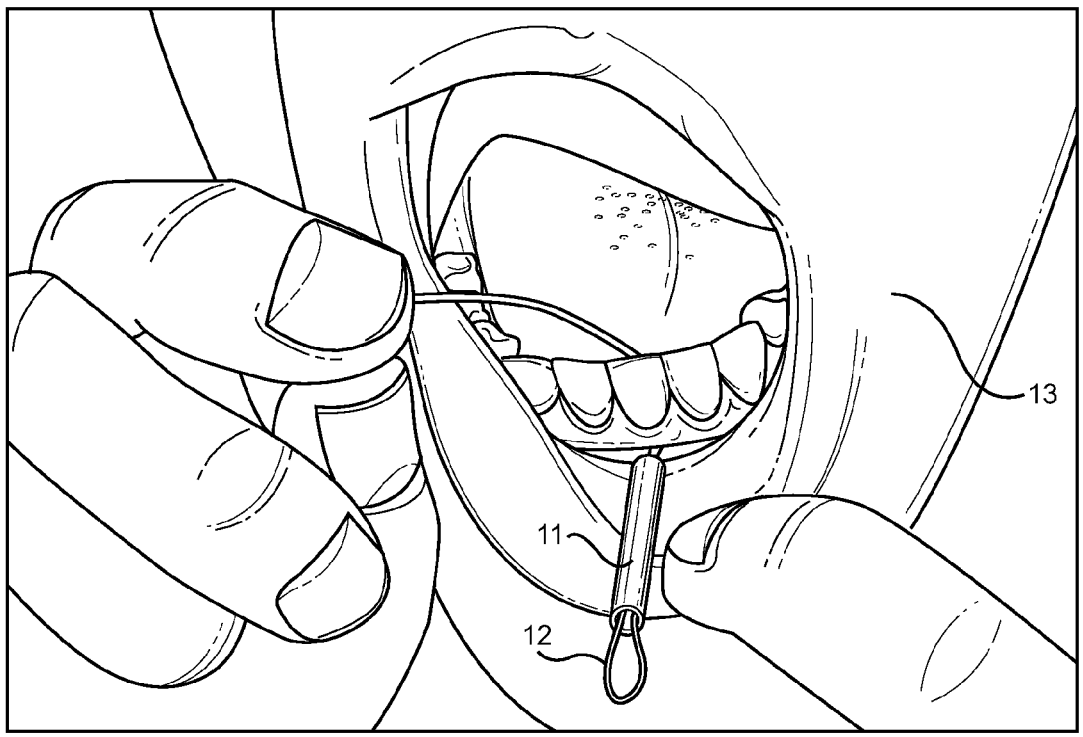
FIG. 3 is a perspective view of the present invention as a user removes the guiding tube from the loop end of the threading line.

Referring now to FIG. 3, there is shown a perspective view of the user removing the guiding tube 11 from the closed-loop end of the threading line 12. To remove the guiding tube, the user 13 must firmly hold the closed end of the threading line 12 that is located within the user's mouth while gently pulling the guiding tube 11 from the threading line 12 by traversing the tube 11 over the loop end of the threading line 12.

Figure 4:
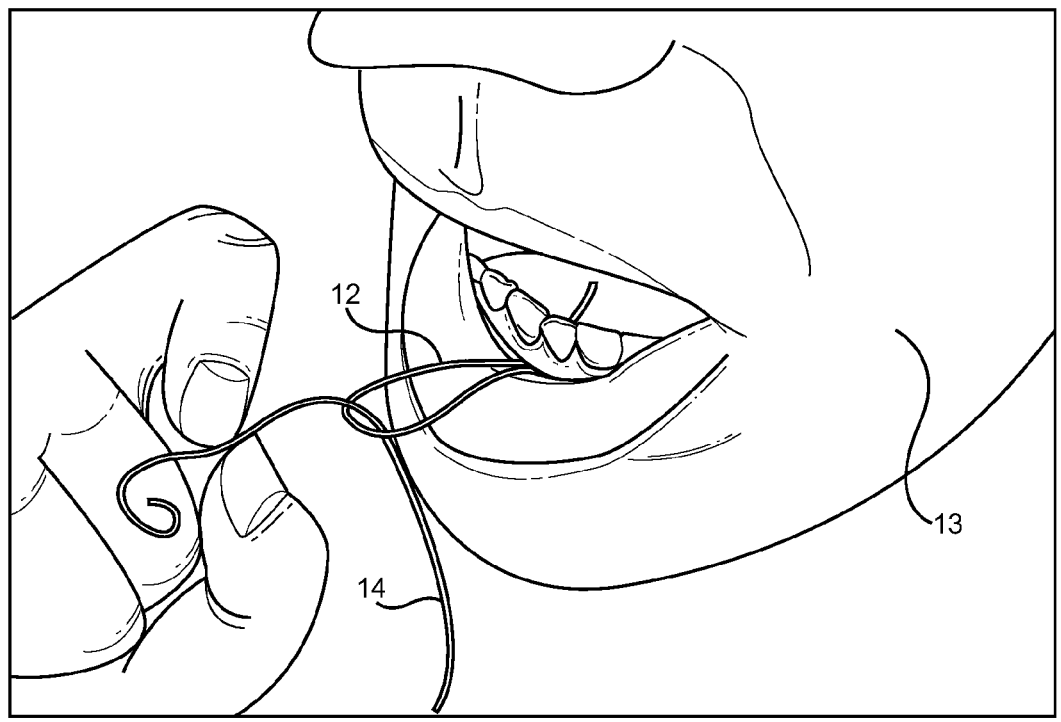
FIG. 4 is a perspective view of the present invention depicting a user inserting dental floss into the loop end of the threading line prior to being pulled through the desired space between teeth or below a set of dentures.

Referring now to FIG. 4, there is shown a perspective view of the user inserting the dental floss variety of his or her choice through the threading line 12 loop end of the device. Once dental floss 14 has been threaded through the threading line loop, the user 13 may gently pull on the non-loop end of the threading line until the loop end of the threading line 12 and the dental floss have been pulled through the space requiring flossing, whether the space be between the user's dentures and the gum line, or between the teeth of a user.

The present invention can also be used to floss between the teeth of a user. The present invention would be very useful for those individuals who wear braces or have permanent retainers cemented to their teeth which inhibits a user's ability to floss in a traditional fashion. The user can use the present invention to floss the space in between teeth and between the implant and the gum line. Use of the present invention greatly facilities the ability of a user to thread flossing through cavities between teeth and between oral implants that would otherwise be difficult or inaccessible. This allows the user to maintain oral hygiene despite oral implants or closely spaced teeth that are difficult to floss.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method for inserting dental floss into a crevice within a mouth, comprising the steps of:
   inserting a length of dental floss into a closed loop at one end of a floss threading line, wherein said floss threading line has a non-loop end distal from said closed loop end;
   inserting said non-loop end of said floss-threading line into a guiding tube;
   placing an end of said guiding tube that is proximal to the inserted floss threading line up to an open space where said floss threading line is to be inserted within a user's oral cavity;
   pushing said closed loop end of said floss threading line through said guiding tube until said non-loop end of said floss threading line passes through said open space;
   pulling on said non-loop end of said floss threading line until said closed loop end passes through said open space along with a portion of said dental floss;
   removing said floss-threading line from said user's oral cavity, leaving behind said dental floss.

2. The method of claim 1, wherein said open space is located between a user's gum line and a lower edge of an oral implant.

3. The method of claim 1, further comprising the step of:
   removing any portion of said dental floss remaining in said guiding tube from said guiding tube after removing said floss-threading line.

4. A method of flossing between a dental implant and the gum line, comprising the steps of:
   inserting a length of dental floss into a closed loop at one end of a floss threading line, wherein said floss threading line has a non-loop end distal from said closed loop end;
   inserting said non-loop end of said floss-threading line into a guiding tube;
   placing an end of said guiding tube that is proximal to the inserted floss threading line up to an open space between an oral implant and a user's gum line;
   pushing said closed loop end of said floss threading line through said guiding tube until said non-loop end of said floss threading line passes through said open space;
   pulling on said non-loop end of said floss threading line until said closed loop end passes through said open space along with a portion of said dental floss;
   removing said floss-threading line from said user's oral cavity, leaving behind said dental floss;
   grasping opposing ends of said floss;
   cleaning said open space with said floss.

* * * * *